(12) United States Patent
Nakamura

(10) Patent No.: US 6,669,684 B2
(45) Date of Patent: Dec. 30, 2003

(54) CORNEAL SURGERY APPARATUS

(75) Inventor: Takua Nakamura, Hoi-gun (JP)

(73) Assignee: Nidek Corp., Ltd. (JP)

( * ) Notice: Subject to any disclaimer, the term of this patent is extended or adjusted under 35 U.S.C. 154(b) by 0 days.

(21) Appl. No.: 09/940,935

(22) Filed: Aug. 29, 2001

(65) Prior Publication Data

US 2002/0026180 A1 Feb. 28, 2002

(30) Foreign Application Priority Data

Aug. 31, 2000 (JP) ........................................ 2000-268437

(51) Int. Cl.$^7$ ................................................ A61B 18/18
(52) U.S. Cl. ................................ 606/5; 606/4; 606/10; 606/11; 606/12; 351/208; 351/211; 351/212
(58) Field of Search ........................... 606/4–6, 10–12; 351/208–212

(56) References Cited

U.S. PATENT DOCUMENTS

| | | | | |
|---|---|---|---|---|
| 5,116,114 A | * | 5/1992 | Nakamura et al. | 351/205 |
| 5,350,374 A | * | 9/1994 | Smith | 606/5 |
| 5,500,697 A | | 3/1996 | Fujieda | |
| 5,507,799 A | | 4/1996 | Sumiya | |
| 5,562,656 A | | 10/1996 | Sumiya | |
| 5,569,238 A | | 10/1996 | Shei | |
| 5,620,437 A | * | 4/1997 | Sumiya | 606/5 |
| 5,637,109 A | | 6/1997 | Sumiya | |
| 5,713,892 A | | 2/1998 | Shimmick | |
| 5,800,424 A | | 9/1998 | Sumiya | |
| 6,004,313 A | * | 12/1999 | Shimmick et al. | 606/5 |
| 6,033,075 A | | 3/2000 | Fujieda | |
| 6,159,202 A | | 12/2000 | Sumiya | |
| 6,245,058 B1 | * | 6/2001 | Suzuki | 606/2 |
| 6,419,671 B1 | * | 7/2002 | Lemberg | 606/5 |

FOREIGN PATENT DOCUMENTS

| | | |
|---|---|---|
| EP | 0 628 298 A1 | 12/1994 |
| EP | 0 811 352 A2 | 12/1997 |
| WO | WO 92/01417 | 2/1992 |

\* cited by examiner

*Primary Examiner*—Linda C. M. Dvorak
*Assistant Examiner*—Ahmed Farah
(74) *Attorney, Agent, or Firm*—Rader, Fishman & Grauer PLLC

(57) ABSTRACT

A corneal surgery apparatus, for ablating a cornea with a laser beam to correct a refractive error more precisely, includes an ablation amount computing device for obtaining an ablation amount of the cornea for each of plural ablation steps based on a refractive error, a determining device for determining laser irradiation control data for each of the ablation steps based on the ablation amount, a corneal shape measurement device including a projecting optical system for projecting a target on the cornea, a photographing optical system for photographing an image of corneal reflection of the target, and a shape computing device for obtaining a corneal shape by processing the photographed target image, and a correcting device for comparing a predetermined ablation amount with an actual ablation amount based on the corneal shape measured after laser irradiation and for correcting the control data for the next step based on the comparison result.

8 Claims, 6 Drawing Sheets

CORNEAL SURGERY APPARATUS

BACKGROUND OF THE INVENTION

1. Field of the Invention

The present invention relates to a corneal surgery apparatus for correcting a refractive error of a patient's eye by ablating a cornea of the patient's eye with a laser beam.

2. Description of Related Art

It has been known that a laser corneal surgery apparatus for ablating a cornea of a patient's eye with an excimer laser beam is used to change a refractive power of the cornea for correcting a refractive error such as myopia, hyperopia, astigmatism, and the like. For such a keratorefractive surgery, PRK (photorefractive keratectomy) and LASIK (laser assisted in-situ keratomileusis) are usually carried out. In PRK, a laser beam is irradiated after peeling an epithelium off, and in LASIK, a laser beam is irradiated to ablate a corneal stroma after a flap is formed by incising the part from the epithelium up to the corneal stroma in a layered form, where the flap is replaced after the irradiation.

Also, as to a keratorefractive surgery performed by this type of the apparatus, an ablation amount of a cornea is determined from the data for correcting a refractive error such as a corneal shape which is obtained before an operation, refractive power to be corrected, and a size of an optical zone, and then a laser beam is irradiated in accordance with the determined ablation amount. And, a corneal shape is generally measured with an apparatus in which a placido ring target is projected on a cornea to detect a mirror surface reflected image on the cornea. Such a measurement apparatus is separated from a surgery apparatus.

However, measurement of the corneal shape by using the mirror surface reflected image is incapable of measuring the corneal shape just before laser irradiation (after the epithelium is peeled off in PRK, and after the flap is formed in LASIK) and soon after laser irradiation. Accordingly, it is impossible to know whether the cornea is ablated in accordance with the determined ablation amount. Therefore, measurement of refractive power before and after the operation is conventionally conducted to judge whether the operation is successful. When the desired correction has not been made, another operation is performed after the eye of the patient heals. This is a burden to the patient.

SUMMARY OF THE INVENTION

The present invention has been made in view of the above circumstances and has an object to overcome the above problems and to provide a corneal surgery apparatus with which an operation can be performed more precisely with improved accuracy in correcting a refractive error by keratectomy.

To achieve the objects and in accordance with the purpose of the present invention, as embodied and broadly described herein, a corneal surgery apparatus ablating a cornea with a laser beam comprises ablation amount computing means for obtaining an ablation amount of the cornea for each of plural ablation steps based on a refractive error of an eye to be operated, determining means for determining laser irradiation control data for each of the ablation steps based on the ablation amount for each of the ablation steps obtained by the ablation amount computing means, corneal shape measurement means including a projecting optical system for projecting a target for measuring a corneal shape on the cornea, a photographing optical system for photographing an image of corneal reflection of the target projected on the cornea, and shape computing means for obtaining a corneal shape by processing the photographed target image, and correcting means for comparing a predetermined ablation amount with an actual ablation amount for a certain ablation step based on the corneal shape measured after laser irradiation at the ablation step and for correcting the laser irradiation control data for a next ablation step based on a result of the comparison.

In another aspect of the present invention, a corneal surgery apparatus ablating a cornea with a laser beam comprises a laser source emitting a laser beam, an irradiation optical system for irradiating the laser beam emitted from the laser source on the cornea, a projecting optical system having a light source and a target plate, for projecting a target for measuring a corneal shape on the cornea, a photographing optical system having a photographic element, for photographing an image of corneal reflection of the target projected on the cornea, a first computing unit which obtains a corneal shape by processing the photographed target image, a second computing unit which obtains an ablation amount of the cornea for each of plural ablation steps based on a refractive error of an eye to be operated, determines laser irradiation control data for each of the ablation steps based on the ablation amount of each of the ablation steps, further compares a predetermined ablation amount with an actual ablation amount for a certain ablation step based on the corneal shape obtained after the laser irradiation at the ablation step, and corrects the laser irradiation control data for a next ablation step based on a result of the comparison, and control unit which controls the irradiation optical system based on the determined laser irradiation control data and the corrected laser irradiation control data.

Yet, in another aspect of the present invention, a corneal surgery apparatus ablating a cornea with a laser beam comprises a laser source emitting the laser beam, an irradiation optical system for irradiating the emitted laser beam on the cornea, a projecting optical system having a light source and a target plate on which a slit is formed, for projecting a slit-shaped target for alignment on the cornea to perform alignment of the apparatus in a direction related to a distance to the cornea, a moving unit which moves the projecting optical system in the direction related to the distance to the cornea at a specified step, a photographing optical system for photographing an image of corneal reflection of the target projected on the cornea, a detecting unit which detects an alignment condition in the direction related to the distance to the cornea by processing the photographed target image, and a computing unit which obtains a corneal shape by processing the photographed target image.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
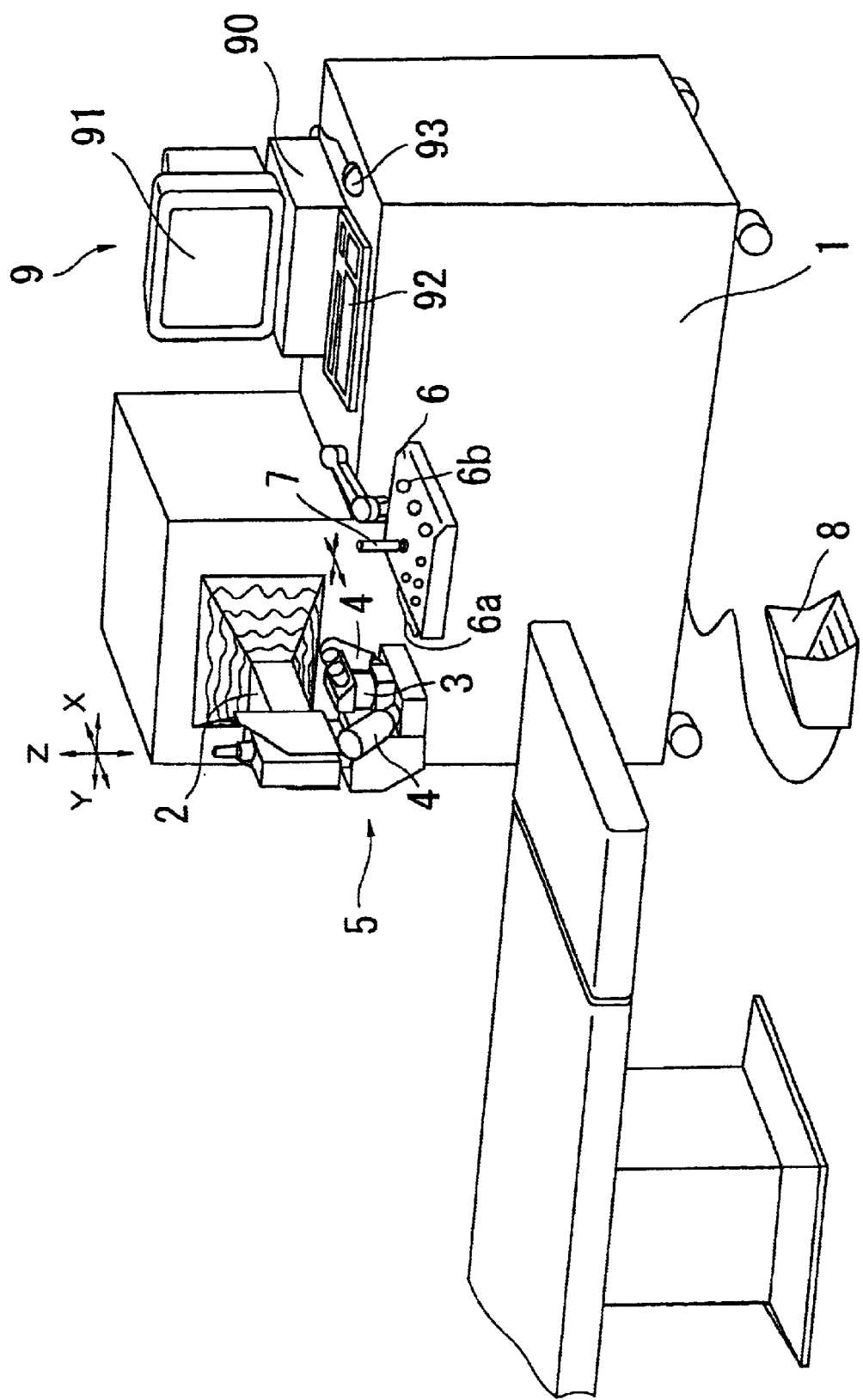
FIG. 1 is an external view of a corneal surgery apparatus consistent with one preferred embodiment of the present invention.
Figure 3:
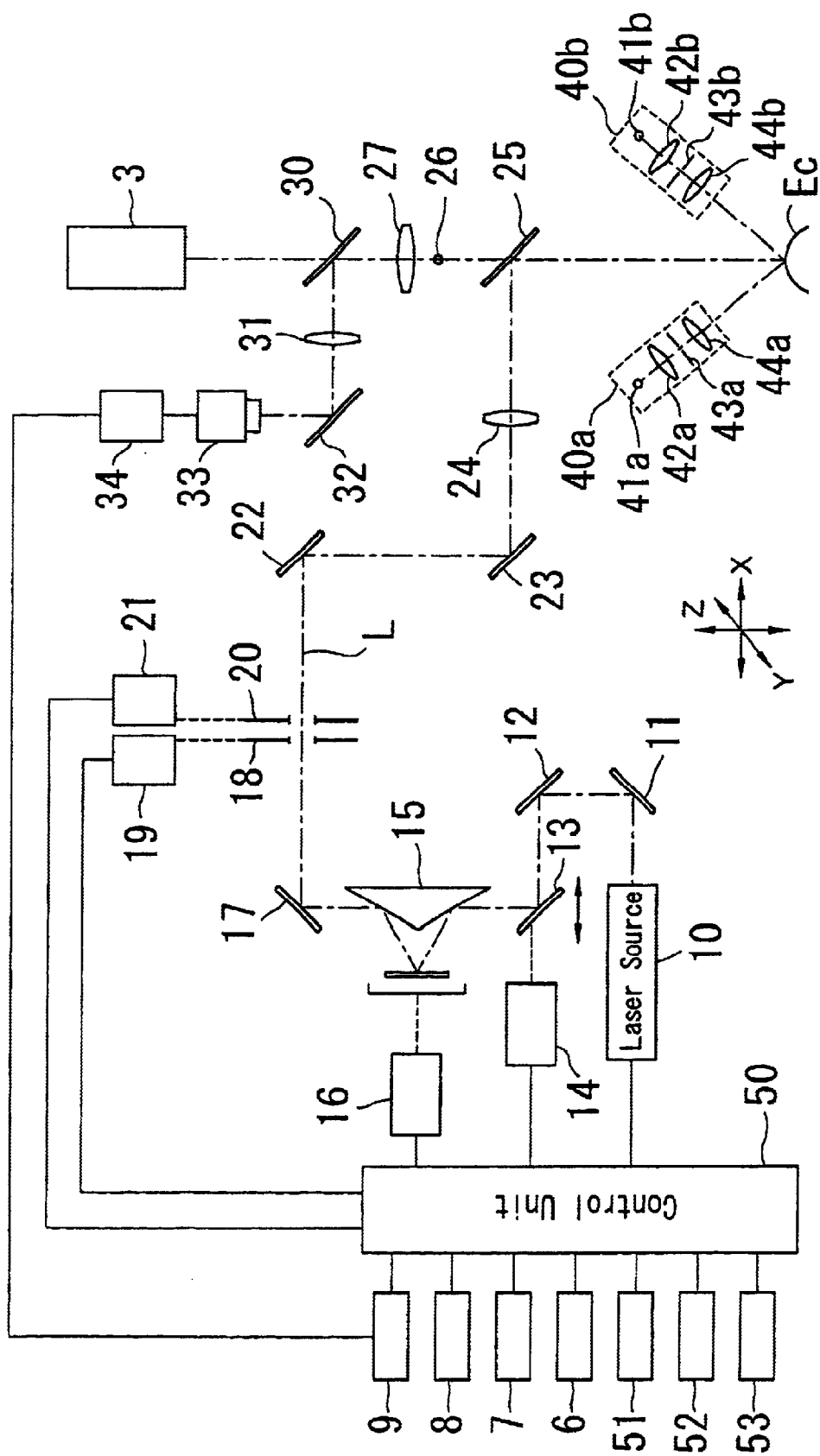
FIG. 3 is a view showing a schematic configuration of an optical system and a control system.

A detailed description of one preferred embodiment of a corneal surgery apparatus embodying the present invention will now be given referring to the accompanying drawings. FIG. 1 is an external view of the corneal surgery apparatus for correcting a refractive error with a laser beam. FIG. 3 is a view showing a schematic configuration of an optical system and a control unit of the present apparatus.

Reference numeral 1 is a main body of the apparatus in which a laser source 10 and the like are embedded. A laser beam emitted from the laser source 10 is led to an arm unit 2 by a laser irradiation optical system disposed in the main body 1 which will be described later (an optical element such as a mirror and the like is disposed inside the arm unit 2). An end portion 5 of the arm unit 2 includes a binocular microscope unit 3 to observe a patient's eye and an illumination unit 4.

Figure 2:
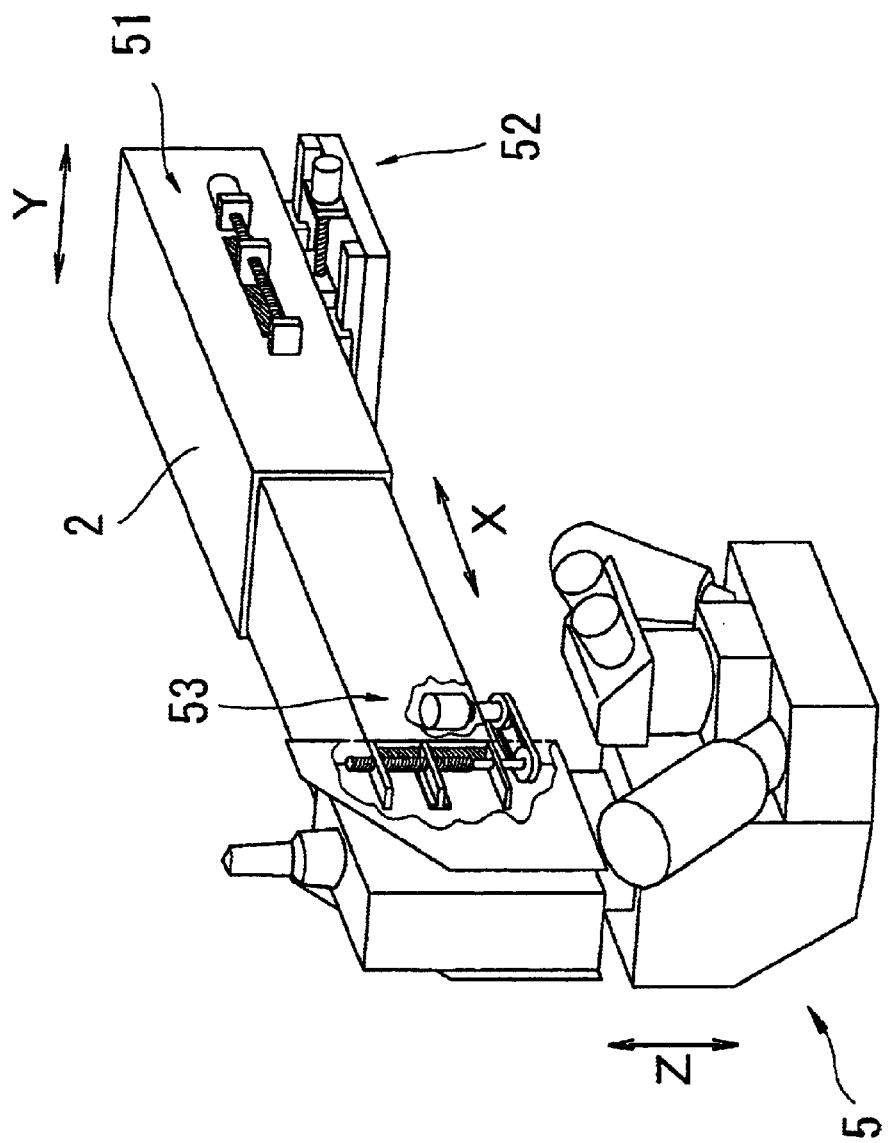
FIG. 2 is a view showing a schematic configuration of an X- and Y-direction arm driving units and a Z-direction end portion driving unit.

As shown in FIG. 2, the arm unit 2 is movable in an X direction (right-and-left direction toward an operator) by an X-direction arm driving unit 51 and in a Y direction (back-and forth direction toward the operator) by a Y-direction arm driving unit 52. Also, the end portion 5 is movable in a Z direction, that is, an up-and-down direction equal to a direction related to the distance between the end portion 5 and a cornea Ec. Each of the driving units 51, 52, and 53 is constituted of a motor and a sliding mechanism.

Reference numeral 6 is a controller including a joystick 7 for giving a signal to a control unit 50 so as to move the arm unit 2 in the X and Y directions, a focus adjustment switch 6a for giving a signal to the control unit 50 so as to move the end portion 5 in the Z-direction, a corneal shape measurement commencing switch 6b, and the like. Reference numeral 8 is a foot switch for giving a signal for commencing laser irradiation to the control unit 50. Reference numeral 9 is a computer for inputting necessary data of various conditions for an operation, as well as for computing, displaying, and storing irradiation control data. The computer 9 is constituted of a main unit 90, a monitor 91, a keyboard 92, a mouse 93, and the like.

Reference numeral 10 is the laser source emitting an excimer laser beam having wavelengths of 193 nm. The laser beam emitted from the laser source 10 is reflected by mirrors 11 and 12, and then it is further reflected by a mirror 13. The mirror 13 may be moved by a mirror driving unit 14 in a direction of an arrow indicated in FIG. 3. In such a manner, the laser beam makes a parallel movement in the direction of the Gaussian distribution of the laser beam so as to ablate an object evenly. The details of this mechanism are disclosed in U.S. Pat. No. 5,507,799 (corresponding to Japanese Unexamined Patent Publication No. HEI4-242644) to be referred.

Reference numeral 15 is an image rotator which is rotatably driven about a central optical axis L by an image rotator driving unit 16 so that the laser beam rotates around the optical axis L. Reference numeral 17 is a mirror. Reference numeral 18 is a circular aperture by which an area of ablation (area of irradiation) is limited to a circular shape, and an aperture diameter is changed by an aperture driving unit 19. Reference numeral 20 is a slit aperture by which the area of ablation (area of irradiation) is limited to a slit shape, and the width and the direction of the slit aperture can be changed by an aperture driving unit 21. Reference numerals 22 and 23 are mirrors. Reference numeral 24 is a projecting lens for projecting images of the circular aperture 18 and the slit aperture 20 on a cornea Ec of a patient's eye. Reference numeral 25 is a dichroic mirror having a characteristic of reflecting the excimer laser beam with wavelengths of 193 nm and transmitting visible light. The laser beam having passed through the lens 24 is deflected by the dichroic mirror 25 to be irradiated (led) to the cornea Ec.

A fixation light 26, an objective lens 27, and the microscope unit 3 are disposed above the dichroic mirror 25. Reference numeral 30 is a mirror disposed on an optical path between the binoculars of the microscope unit 3. An image forming lens 31, a mirror 32, and a CCD camera 33 are provided on an optical path opposite to the mirror 30. The camera 33 is connected with an image analyzing unit 34 providing an analytical result of a corneal shape which is inputted in the computer 9, as will be described later.

Below the dichroic mirror 25, slit projecting optical systems 40a and 40b are provided in the illumination unit 4, and they are disposed at positions diametrically opposed to each other with respect to the optical axis of the lens 27 in-between. These projecting optical systems 40a and 40b are used not only as an optical system for projecting a target for alignment in the Z-direction but also as an optical system for projecting a target for corneal shape measurement. Each of the projecting optical systems 40a and 40b is constituted of illumination lamps 41a and 41b emitting visible light, condenser lenses 42a and 42b, slit plates 43a and 43b each having a cross-shaped slit, and projecting lenses 44a and 44b, respectively. It is not necessary that the slit plates 43a and 43b have a cross-shaped slit, and they may have a slit in other shapes. The slit plates 43a and 43b are at a position conjugate with the cornea Ec with respect to the lenses 44a and 44b, and it is arranged that an image of the cross-shaped slit (image of the slit target) should be always formed at a focal point on the optical axis of the lens 27. Furthermore, a photographing surface of the camera 33 is made to be conjugate with the focal point on the optical axis of the lens 27 by the lens 31, and the camera 33 is used as a detecting system of the image of the slit target.

Reference numeral 50 is the control unit controlling the laser source 10 and each driving unit. Also, the computer 9 and more are connected with the control unit 50.

It is preferable that an eye tracking mechanism (mechanism for tracking the movement of the eye to adjust the point of laser irradiation when the patient's eye moves during alignment or laser irradiation) be provided in the present apparatus although the mechanism is not illustrated in the figure of the present embodiment. The details about this mechanism are disclosed in U.S. Pat. No. 6,159,202 (corresponding to Japanese Unexamined Patent Publication No. HEI9-149914) to be referred.

Next, operation of the present apparatus will be described. A description will be provided on the assumption that a spherical correction of myopia is carried out.

First, data of conditions for an operation such as refractive power to be corrected and a size of an area of ablation are inputted to the computer 9. Then, the computer 9 obtains data of an ablation amount based on the inputted data. When PRK is carried out, the operator peels an epithelium of the cornea Ec before laser irradiation.

While the operator observes an image of an anterior part of the patient's eye with the microscope unit 3, he/she operates the joystick 7 to move the arm unit 2 in the X and Y directions for alignment so that a reticle and a pupil, which are not illustrated, bear a specific relation. Also, the operator operates the switch 6a to move the end portion 5 up and down for alignment in the Z direction.

Figure 4A:
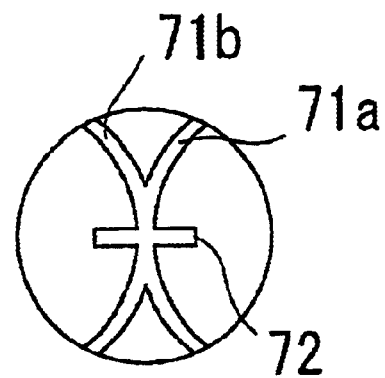
FIG. 4A is a view showing slit lines when alignment between an end portion of an arm unit and a cornea in the Z-direction is appropriate.
Figure 4B:
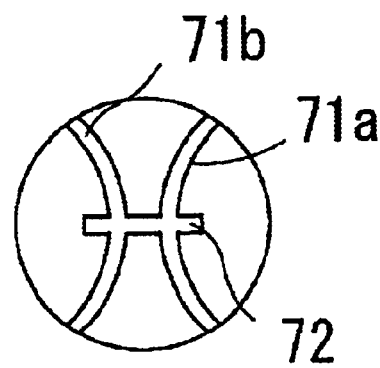
FIG. 4B is a view showing the slit lines when the alignment between the end portion and the cornea in the Z-direction is not appropriate.
Figure 4C:
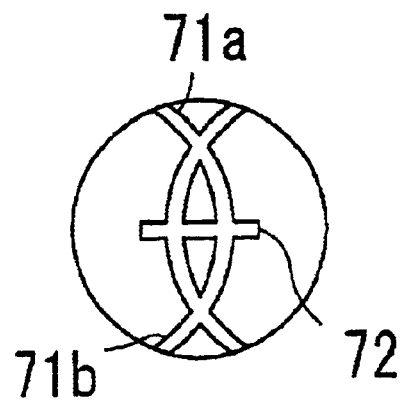
FIG. 4C is a view showing the slit lines when the alignment between the end portion and the cornea in the Z-direction is not appropriate.

The alignment in the Z direction, for which the images of the slit targets projected by the projecting optical systems 40a and 40b are observed, will be carried out in the following way. Most part of the slit target from the projecting optical system 40a on the left in FIG. 3 transmits the cornea Ec, but some part of the slit target scatters on the cornea Ec and is observed as an arc-shaped slit line (image) 71a in FIG. 4A through the microscope unit 3. Likewise, the slit target from the projecting optical system 40b on the right is observed as an arc-shaped slit line (image) 71b in FIG. 4A (reference numeral 72 is a crossing line (image) intersecting at right angles with the slit lines 71a and 71b in the center). When the apex of the cornea Ec is at the focal point of the microscope unit 3, the slit line 71a from the left and the slit line 71b from the right overlap at the point of the corneal apex as illustrated in FIG. 4A. However, when the cornea Ec is farther from the end portion 5 than the focal point, the two slit lines 71a and 71b are observed to be separated as illustrated in FIG. 4B. Also, when the cornea Ec is closer to the end portion 5 than the focal point, the two slit lines 71a and 71b are observed to intersect as illustrated in FIG. 4C. Accordingly, the end portion 5 is moved downward in the case of FIG. 4B, and it is moved upward in the case of FIG. 4C. In such a manner, the focal point of the microscope unit 3 can be positioned on the cornea Ec by changing the alignment condition in the Z-direction so that the slit lines 71a and 71b show the shape illustrated in FIG. 4A.

After the completion of the alignment, the operator presses the switch 6b to measure the corneal shape before laser irradiation. Preferably, the apparatus automatically commences the measurement by detecting the shape illustrated in FIG. 4A. The slit lines 71a and 71b are photographed by the camera 33, and the image is inputted to the image analyzing unit 34. Also, the control unit 50 sequentially moves the end portion 5 upward and downward in the Z-direction by a specified amount with reference to a position of alignment, and the image analyzing unit 34 obtains an image photographed by the camera 33 in each movement.

Figure 5A:
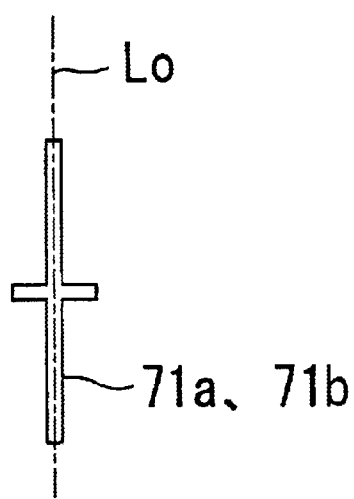
FIG. 5A is a view showing the slit lines projected on a flat plate when the alignment between the end portion and the cornea in the Z-direction is appropriate.
Figure 5B:
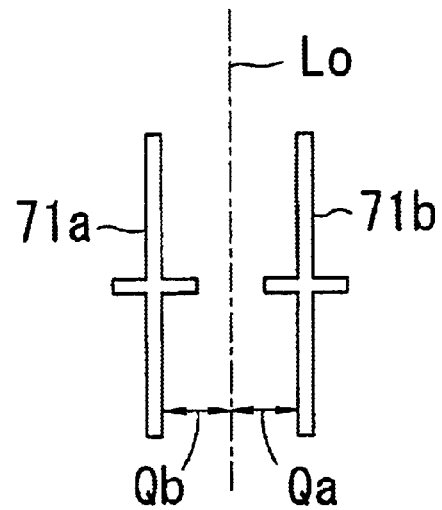
FIG. 5B is a view showing the slit lines projected on the flat plate when the alignment between the end portion and the cornea in the Z-direction is not appropriate.

A method of measuring a corneal shape by using slit lines 71a and 71b will be described. When the slit targets from the projecting optical systems 40a and 40b are projected on a flat plate, the two slit lines 71a and 71b overlap on a central axial line Lo illustrated in FIG. 5A if the flat plate is at a reference height point (focal point). On the other hand, when the flat plate is below the reference height point, the two slit lines 71a and 71b are observed to be apart from the central axial line Lo as illustrated in FIG. 5B. At this point, a distance Qa of the slit line 71a and a distance Qb of the slit line 71b from the central axial line Lo vary in proportion to a gap between the flat plate and the reference height point in a vertical direction (z-direction).

Figure 6:
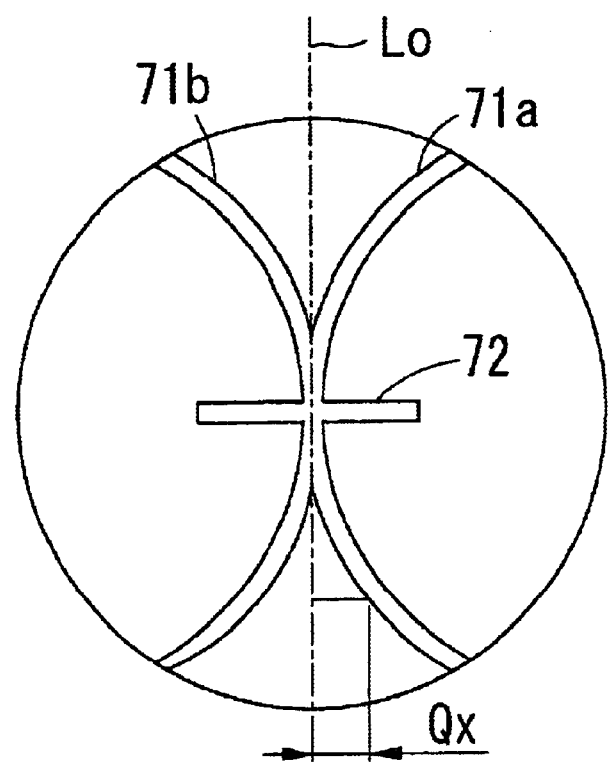
FIG. 6 is view showing the slit lines projected on the cornea.

When these slit targets are projected on the cornea Ec which is approximately spherical, the shape of the slit lines becomes curves as illustrated in FIG. 6. In FIG. 6, information about corneal heights at many points on the slit line 71a can be obtained by sequentially determining (detecting) a distance Qx between the central axial line Lo and an inner edge of the slit line 71a. Then, when the position of projecting the slit target on the cornea Ec is moved up and down, coordinates of the slit lines 71a and 71b change as illustrated in FIG. 4B and 4C mentioned above. Accordingly, it is possible to obtain the information about the height at each point on the cornea Ec. To carry out this computation, it is necessary to make a correction to compensate a movement amount of the end portion 5 for moving the position of projecting the slit target up and down.

By following such processes, after the image analyzing unit 34 analyzes the image of the slit targets, the computer 9 obtains the corneal shape based on the information about the corneal height at each set of the coordinates. The photographed image includes the image of the slit targets scattering on an iris, but image processing distinguishes it from the image of the slit targets scattering on the cornea Ec in accordance with differences in a positional relation, luminance, and the like between two images.

After measuring the corneal shape, the operator operates the foot switch 8 for commencing laser irradiation. For myopic correction, the circular aperture 18 limits an irradiation area of the laser beam, and the laser beam is moved in the direction of the Gaussian distribution by sequentially moving the mirror 13. Then, every time the laser beam finishes performing one scan, the image rotator 15 rotates to change a direction of a laser beam movement (for example, in three directions each having space of 120 degrees), and the laser beam approximately evenly ablates the area limited by the circular aperture 18. By repeating this process every time the diameter of the circular aperture 18 is changed in sequence, it is possible to perform myopic correction enlarging a radius of curvature of the cornea Ec (refer to U.S. Pat. No. 637,109 corresponding to Japanese Unexamined Patent Publication No. HEI6-114083).

According to the present preferred embodiment, the subject apparatus is programmed such that laser irradiation should be executed with two separate steps. For example, it is set that 70% of a total predetermined ablation amount (correction amount) should be ablated by laser irradiation at the first step. After the completion of the first step of the laser irradiation, the operator performs alignment and presses the switch 6b to measure the corneal shape in the same way as described above. When the computer 9 obtains the corneal shape after the laser irradiation, it computes an actual ablation amount by subtracting the corneal shape after the laser irradiation from the corneal shape before the laser irradiation. Then, by comparing the predetermined ablation amount of the laser irradiation at the first step to the actual ablation amount of the laser irradiation at the first step, a predetermined ablation amount of laser irradiation at the second step is obtained based on a result of the comparison. In accordance with data of the comparison, the irradiation control data for the laser irradiation at the second step are corrected.

How to compute the predetermined ablation amount of the laser irradiation at the second step will be described. When St is a total predetermined ablation amount, S1 is the predetermined ablation amount of the laser irradiation at the first step, and S1' is the actual ablation amount at the first step, a ratio of an ablation error K by laser irradiation at the first step is obtained according to the following formula:

$$K=S1'/S1.$$

The ablation amount for the laser irradiation at the second step is obtained from St−S1'. If an ablation error occurs at the same ratio of the ablation error K in the laser irradiation at the second step, a predetermined ablation amount Sx, which should be set for the laser irradiation at the second step, can be determined according to the following formula:

$$Sx=(St-S1')/K.$$

In such a manner, after the predetermined ablation amount Sx for the laser irradiation at the second step is obtained, the operator operates the foot switch 8 again so that the computer 9 gives the control unit 50 the irradiation control data corrected for ablating the cornea Ec by the predetermined ablation amount Sx, and the control unit 50 controls the laser source 10 and each driving unit. The aperture diameter of the circular aperture 18 is limited by converting the predetermined ablation amount Sx into refractive power in order to control the laser irradiation. Differently, the aperture diameter of the circular aperture 18 can be also limited in accordance with a depth of ablation at each point determined from the predetermined ablation amount Sx. Since the laser irradiation at the second step is executed with consideration for the error resulting from the laser irradiation at the first step, it is possible to perform an operation in which the cornea Ec is ablated nearly by the set total predetermined ablation amount.

After the laser irradiation at the second step and realignment, the corneal shape is measured in the same way as described above. By displaying a result on the monitor 91, the operator can determine whether the operation is successful. When the ablation amount (correction amount) is not enough at this point, it is possible to successively execute laser irradiation.

In the keratorefractive surgery described above, the procedure of laser irradiation can be divided into more than two ablation steps. In such cases, the corneal shape is measured after laser irradiation at a certain step, and the irradiation control data for the next step are corrected in the same way as described above.

A description of myopic correction has been provided so far, but the same procedure can be applied to hyperopic correction and astigmatic correction.

Also, the description of PRK is provided above, but in the case of LASIK, after forming a flap, the corneal shape before and after executing laser irradiation is measured in the same way disclosed above so as to give feedback to the next laser irradiation.

In addition, the optical system for corneal shape measurement consistent with the embodiment mentioned above may be provided with a mechanism by which the projecting optical systems 40a and 40b are rotated about the optical axis of the lens 27, whereby the entire shape of the cornea Ec is measured by sequentially changing an angle of projecting the slit target and by photographing an image of the slit target.

Figure 7:
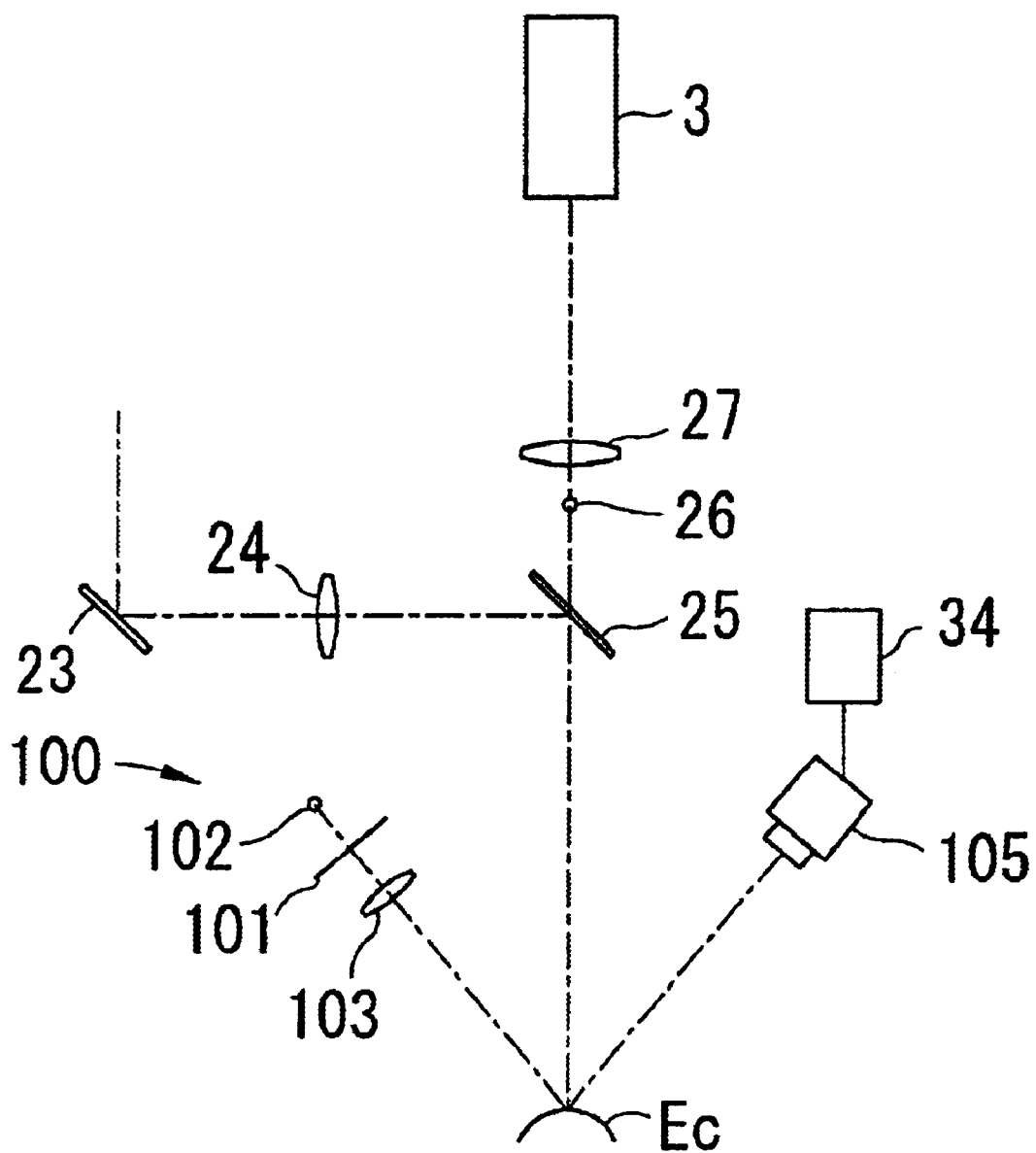
FIG. 7 is a view showing a schematic configuration of another embodiment of an optical system for corneal shape measurement.

Furthermore, it is not necessary that the optical system for corneal shape measurement doubles as the projecting optical systems 40a and 40b for projecting a target for alignment, and it can be separately disposed. For example, in FIG. 7, reference numeral 100 is an optical system for projecting a target for measuring a corneal shape, and reference numeral 101 is a target plate on which a small grid pattern (including a dot-like grid pattern) is formed. The target plate 101 is illuminated by an illumination light source 102 disposed behind the plate 101, and an image of the grid pattern target is formed at the focal point on the optical axis of the objective lens 27 by a projecting lens 103. A CCD camera 105 is provided on an optical axis diametrically opposed to the optical axis of the projecting optical system 100 with respect to the optical axis of the lens 27 in-between. The CCD camera 105 is used to photograph the image of the grid pattern target projected on the cornea Ec. At the time of measurement, fluorescein is dropped into the eye to create a screen state on the cornea Ec so that the image of the grid pattern target projected on the cornea Ec is observed. The image analyzing unit 34 measures the corneal shape by detecting changes in spacing on the grid pattern in the image photographed with the camera 105. This kind of measurement optical system is capable of measuring the entire cornea Ec by analyzing one photographed image. Also, to prevent a slit target for alignment which is not illustrated in the figure from becoming a noise, the lamps 41a and 41b of the projecting optical systems 40a and 40b are turned off at the time of measurement.

In the embodiment described above, the so called slit scan method as the method of irradiating a laser beam is employed, but the spot scan method, the one-shot irradiation method, or a method obtained by modifying those three methods can be employed.

As described above, according to the present invention, an operation can be performed more precisely with improved accuracy in correcting a refractive error by keratectomy.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A corneal surgery apparatus for ablating a cornea of an eye to be operated with a laser beam comprising:

ablation means having an irradiation optical system, for ablating the cornea by irradiation of the laser beam;

ablation amount computing means for obtaining a total ablation amount of the cornea based on a refractive error of the eye and for separating the total ablation amount into at least first and second ablation amounts by a predetermined ratio;

determining means for determining first and second control data for first and second ablation by the ablation means based on the first and second ablation amounts respectively;

control means for controlling the first ablation based on the first control data;

corneal shape measurement means including
      a projecting optical system for projecting an image of a target for measuring a corneal shape on the cornea, a photographing optical system for photographing the target image projected on the cornea, and shape computing means for obtaining the corneal shape by processing the photographed target image; and correcting means for comparing the first ablation amount with an actual ablation amount resulted by the first ablation and obtained based on the corneal shapes measured before and after the first ablation and for correcting the second control data based on a result of the comparison, wherein the control means controls the second ablation based on the corrected second control data.

2. The corneal surgery apparatus according to claim 1, 1 wherein the projecting optical system projects an image of a slit target as the target image for measuring the corneal shape, the corneal shape measurement means includes moving means for moving the projecting optical system in a direction related to a distance to the cornea at a specified step, and the photographing optical system photographs the slit target image at each position to which the projecting optical system is moved by the moving means.

3. The corneal surgery apparatus according to claim 1, wherein the projecting optical system projects an image of a grid pattern target as the target image for measuring the corneal shape on the cornea.

4. The corneal surgery apparatus according to claim 1, wherein the projecting optical system doubles as an optical system for projecting an image of a target for alignment to perform alignment of the apparatus in a direction related to a distance to the cornea.

5. A corneal surgery apparatus for ablating a cornea of an eye to be operated with a laser beam comprising:

ablation means having an irradiation optical system, for ablating the cornea by irradiation of the laser beam;

ablation amount computing means for obtaining a total ablation amount of the cornea based on a refractive error of the eye and for obtaining a first ablation amount based on the total ablation amount and a predetermined ratio;

determining means for determining first control data for first ablation by the ablation means based on the first ablation amount;

control means for controlling the first ablation based on the first control data;

corneal shape measurement means including a projecting optical system for projecting an image of a target for measuring a corneal shape on the cornea, a photographing optical system for photographing the target image projected on the cornea; and shape computing means for obtaining the corneal shape by processing the photographed target image; and comparing means for comparing the first ablation amount with an actual ablation amount resulted by the first ablation and obtained based on the corneal shapes measured before and after the first ablation, wherein the ablation amount computing means obtains a second ablation amount based on the total ablation amount, the actual ablation amount and a result of the comparison, the determining means determines second control data for second ablation by the ablation means based on the second ablation amount, and the control means controls the second ablation based on the second control data.

6. The corneal surgery apparatus according to claim 5, wherein the corneal shape measurement means includes a moving unit which moves the projecting optical system in a direction related to a distance to the cornea at a specified step, the projecting optical system projects an image of a slit target as the target image for measuring the corneal shape, and the photographing optical system photographs the slit target image at each position to which the projecting optical system is moved.

7. The corneal surgery apparatus according to claim 5, wherein the projecting optical system projects an image of a grid pattern target as the target image for measuring the corneal shape.

8. The corneal surgery apparatus according to claim 5 wherein the projecting optical system doubles as an optical system for projecting an image of a target for alignment to perform alignment of the apparatus in a direction related to a distance to the cornea.

* * * * *